US010793491B2

(12) United States Patent
Fickel et al.

(10) Patent No.: US 10,793,491 B2
(45) Date of Patent: Oct. 6, 2020

(54) PROCESS FOR PRODUCING BENZENE FROM C5-C12 HYDROCARBON MIXTURE

(71) Applicant: SABIC Global Technologies B.V., Bergen op Zoom (NL)

(72) Inventors: Dustin Fickel, Houston, TX (US); Stephen Hall, Cheshire (GB); Kumar Prashant, Altrincham (GB); Maikel van Iersel, Den Bosch (NL); Sonia Farrokhpanah, Walton on Thames (GB)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 96 days.

(21) Appl. No.: 15/318,154

(22) PCT Filed: Jun. 1, 2015

(86) PCT No.: PCT/EP2015/062075
§ 371 (c)(1),
(2) Date: Dec. 12, 2016

(87) PCT Pub. No.: WO2016/005105
PCT Pub. Date: Jan. 14, 2016

(65) Prior Publication Data
US 2017/0121239 A1   May 4, 2017

(30) Foreign Application Priority Data
Jun. 13, 2014   (EP) .................................... 14172336

(51) Int. Cl.
*C07C 4/06* (2006.01)
*C10G 65/14* (2006.01)
(Continued)

(52) U.S. Cl.
CPC .................. *C07C 4/06* (2013.01); *B01J 29/42* (2013.01); *B01J 29/44* (2013.01); *C07C 4/18* (2013.01);
(Continued)

(58) Field of Classification Search
CPC ................ C07C 4/00–26; C10G 45/00; C10G 47/00–20
See application file for complete search history.

(56) References Cited

U.S. PATENT DOCUMENTS 3,433,848 A     3/1969  Devins
3,770,614 A *  11/1973  Graven .................... B01J 29/40
                                                             208/62
(Continued)

FOREIGN PATENT DOCUMENTS

EP            0704416 A1     4/1996
WO      WO-9400409 A1 *     1/1994  ............. C10G 29/16
(Continued)

OTHER PUBLICATIONS

Bhirud, "Chances for Innovative Processes at the Interface between Refining and Petrochemistry" Proceedings of the DGMK Conference (2002), pp. 115-122.
(Continued)

Primary Examiner — In Suk C Bullock
Assistant Examiner — Alyssa L Cepluch
(74) Attorney, Agent, or Firm — Cantor Colburn LLP (57) ABSTRACT

A process for producing benzene comprising the steps of: (a) separating a source feedstream comprising C5-C12 hydrocarbons including benzene and alkylbenzenes into a first feedstream comprising a higher proportion of benzene than the source feedstream and a second feedstream comprising a lower proportion of benzene than the source feedstream and subsequently,
(Continued)

(b) contacting the first feedstream in the presence of hydrogen with a first hydrocracking catalyst, and
(c) contacting the second feedstream with hydrogen under second process conditions to produce a second product stream comprising benzene, wherein
i) the second process conditions are suitable for hydrocracking and step (c) involves contacting the second feedstream in the presence of hydrogen with a second hydrocracking catalyst,
ii) the second process conditions are suitable for toluene disproportionation and involve contacting the second feedstream with a toluene disproportionation catalyst or
iii) the second process conditions are suitable for hydrodealkylation.

13 Claims, 1 Drawing Sheet

(51) Int. Cl.
| | |
|---|---|
| C10G 65/10 | (2006.01) |
| B01J 29/44 | (2006.01) |
| C10G 45/00 | (2006.01) |
| C07C 4/18 | (2006.01) |
| C07C 6/12 | (2006.01) |
| C10G 47/18 | (2006.01) |
| C10G 45/62 | (2006.01) |
| C10G 65/18 | (2006.01) |
| C07C 7/04 | (2006.01) |
| B01J 29/42 | (2006.01) |

(52) U.S. Cl.
CPC .............. *C07C 6/123* (2013.01); *C07C 7/04* (2013.01); *C10G 45/00* (2013.01); *C10G 45/62* (2013.01); *C10G 47/18* (2013.01); *C10G 65/14* (2013.01); *C10G 65/18* (2013.01); *B01J 2229/18* (2013.01); *B01J 2229/20* (2013.01); *B01J 2229/42* (2013.01); *C07C 2529/44* (2013.01); *C10G 2400/30* (2013.01); *Y02P 20/52* (2015.11)

(56) References Cited

U.S. PATENT DOCUMENTS

| | | | |
|---|---|---|---|
| 3,957,621 A | 5/1976 | Bonacci et al. | |
| 4,503,023 A * | 3/1985 | Breck | B01J 29/06 |
| | | | 423/715 |
| H1305 H * | 5/1994 | Townsend | C10G 35/00 |
| | | | 44/448 |
| 5,689,026 A * | 11/1997 | Wu | B01J 29/7815 |
| | | | 585/418 |
| 6,160,191 A | 12/2000 | Smith et al. | |
| 6,504,074 B2 | 1/2003 | Verduijn et al. | |
| 6,635,792 B2 * | 10/2003 | Choi | B01J 29/068 |
| | | | 208/111.1 |
| 6,977,320 B2 | 12/2005 | Verduijn et al. | |
| 7,304,195 B2 * | 12/2007 | Choi | C10G 21/00 |
| | | | 208/111.1 |
| 8,309,778 B2 * | 11/2012 | Wang | B01J 29/068 |
| | | | 208/137 |
| 2006/0287564 A1 | 12/2006 | Choi et al. | |
| 2012/0067776 A1 | 3/2012 | Diehl et al. | |

FOREIGN PATENT DOCUMENTS

| | | |
|---|---|---|
| WO | 0244306 A1 | 6/2002 |
| WO | 2007055488 A1 | 5/2007 |
| WO | 2008015027 A1 | 2/2008 |
| WO | 2013182534 A1 | 12/2013 |

OTHER PUBLICATIONS

F. Rase, Handbook of Commercial Catalysts: Heterogeneous Catalysts; CRC Press (2000) pp. 211-212.
International Search Report for International Application No. PCT/EP2015/062075; dated Aug. 7, 2015; 5 pages.
Kirk-Othmer Encyclopedia of Chemical Technology, "Molecular Sieves," Fifth Edition, vol. 16, (2006), pp. 811-853.
Le Page, "Applied Heterogeneous Catalysis: Design, Manufacture, Use of Solid Catalysts," (1987) Institut Francais due Petrole Publications; pp. 1-7.
Meyers "Handbook of Petroleum Refining Processes," (1986) McGraw-Hill: Chemical Process Technology Handbook Series; pp. 2-3 to 2-7.
Scherzer et al., Hydrocracking Science and Technology (1996) pp. 13-14 and 174.
Tsai T. et al.; "Disproportionation and transalkylation of alkylbenzenes over zeolite catalysts", Applied Catalysis A: General, 1999, vol. 181, Issue 2, pp. 355-398.
Written Opnion of the International Search Report for International Application No. PCT/EP2015/062075; dated Aug. 7, 2015; 8 pages.
Baerlocher et al.; "Atlas of Zeolite Framework Types"; Elsevier, Fifth Revised Edition, 2001, pp. 1-308.

* cited by examiner

PROCESS FOR PRODUCING BENZENE FROM C5-C12 HYDROCARBON MIXTURE

CROSS REFERENCE TO RELATED APPLICATIONS

This application is a 371 of International Application No. PCT/EP2015/062075, filed Jun. 1, 2015, which claims priority to European Application No. 14172336.1, filed Jun. 13, 2014 both of which are incorporated herein by reference in their entirety.

The present invention relates to a process for producing benzene from a mixed feedstream comprising C5-C12 hydrocarbons by contacting said feedstream in the presence of hydrogen with a catalyst having hydrocracking activity.

It has been previously described in WO 02/44306 A1 and WO 2007/055488 A1 that aromatic hydrocarbon compounds and LPG can be produced from a mixed hydrocarbon feedstock having boiling points of 30-250° C. Therefore a hydrocarbon feedstock having boiling points of 30-250° C. and hydrogen is introduced to a reaction zone wherein said hydrocarbon feedstock is converted in the presence of a catalyst to aromatic hydrocarbon compounds abundant in BTX through hydrodealkylation and/or transalkylation and to non-aromatic hydrocarbon compounds which are abundant in LPG through hydrocracking and recovering the aromatic hydrocarbon compounds and LPG, respectively, through gas-liquid separation and distillation. The catalyst used in the process of WO 02/44306 A1 comprises platinum/tin or platinum/lead and a mixture support consisting of 10-95 wt % of zeolite having a molar ratio of silica/alumina of 200 or less and 5-90 wt % of inorganic binder, said zeolite being selected from the group consisting of mordenite, beta type zeolite, ZSM-5 type zeolite and a mixture thereof, in which said platinum is present at an amount of 0.01-0.5 parts by weight, and said tin is present at an amount of 0.01-5.0 parts by weight or said lead is present at an amount of 0.02-5.0 parts, on the basis of 100 parts by weight of said mixture support. The catalyst used in the process of WO 2007/055488 A1 is prepared by supporting 0.01~0.5 parts by weight of platinum (Pt) and 0.01~3.0 parts by weight of bismuth (Bi) onto 100 parts by weight of a mixture support, the mixture support including 10~95 wt % of zeolite having a molar ratio of silica/alumina of 200 or less, selected from the group consisting of mordenite, beta zeolite, ZSM-5 zeolite and combinations thereof, and 5~90 wt % of an inorganic binder. The methods of WO 02/44306 A1 and WO 2007/055488 are characterized in that the hydrogenation activity of the hydrogenation metal platinum that is comprised in the catalyst must be inhibited by a secondary metal such as tin, lead or bismuth. As a result thereof, the catalyst becomes highly susceptible to deactivation by contaminants and heteroatoms that are often comprised in hydrocarbon feedstocks such as sulphur. The methods of WO 02/44306 A1 and WO 2007/055488 produce a product stream comprising a relatively high amount of non-aromatic hydrocarbons that co-boil with BTX rendering it impossible to produce chemical grade BTX without using solvent extraction methods and a relatively high amount of fuel gas at the expense of the LPG produced.

WO2013/182534 discloses a process for producing BTX from a C5-C12 hydrocarbon mixture using a hydrocracking/hydrodesulphurisation catalyst. According to WO2013/182534, the process results in a mixture comprising substantially no co-boilers of BTX, thus chemical grade BTX can easily be obtained.

While the process of WO2013/182534 advantageously limits the amount of BTX co-boilers in the obtained mixture, control of the ratio between benzene, toluene and xylene in the obtained mixture is limited. In some cases, it is preferred to obtain more benzene than other aromatics such as toluene and xylene.

It would therefore be desirable to provide a process for converting a C5-C12 hydrocarbon feedstream by which chemical grade benzene is obtained, which results in an increased yield of benzene compared to known processes.

It is an object of the present invention to provide a process for converting a mixed C5-C12 hydrocarbon feedstream into a product stream in which above and/or other needs are met.

Accordingly, the present invention provides a process for producing benzene comprising the steps of:
(a) separating a source feedstream comprising C5-C12 hydrocarbons including benzene and alkylbenzenes into a first feedstream comprising a higher proportion of benzene than the source feedstream and a second feedstream comprising a lower proportion of benzene than the source feedstream and subsequently
(b) contacting the first feedstream in the presence of hydrogen with a first hydrocracking catalyst comprising 0.01-1 wt-% hydrogenation metal in relation to the total catalyst weight and a zeolite having a pore size of 5-8 Å and a silica (SiO2) to alumina (Al2O3) molar ratio of 5-200 under first process conditions to produce a first product stream comprising benzene, wherein the first process conditions include a temperature of 425-580° C., a pressure of 300-5000 kPa gauge and a Weight Hourly Space Velocity of 0.1-15 $h^{-1}$, and
(c) contacting the second feedstream with hydrogen under second process conditions to produce a second product stream comprising benzene, wherein
i) the second process conditions are suitable for hydrocracking and step (c) involves contacting the second feedstream in the presence of hydrogen with a second hydrocracking catalyst comprising 0.01-1 wt-% hydrogenation metal in relation to the total catalyst weight and a zeolite having a pore size of 5-8 Å and a silica (SiO2) to alumina (Al2O3) molar ratio of 5-200 under the second process conditions which include a temperature of 425-580° C., a pressure of 300-5000 kPa gauge and a Weight Hourly Space Velocity of 0.1-15 $h^{-1}$,
ii) the second process conditions are suitable for toluene disproportionation and involve contacting the second feedstream with a toluene disproportionation catalyst or
iii) the second process conditions are suitable for hydrodealkylation.

The composition of the hydrocracking product stream, especially the ratio between benzene, toluene and xylene, is determined by the composition of the feedstream as well as the interconversion of aromatics during the hydrocracking of the feedstream. The present invention is based on the insight that the composition of the feedstream can be adjusted to optimize the extent of aromatics interconversion reactions during hydrocracking. Depending on the ratio between different aromatics, in particular the benzene proportion in the feedstreams, the benzene proportion in the product streams can vary. According to the invention, the final amount of benzene obtained can be increased compared to when the original feed stream is subjected to hydrocracking without the prior separation of the feed stream as described in step a). Furthermore, different conditions can be applied to the two feedstreams to optimize the benzene proportion in the product streams. Moreover, according to the invention, high purity benzene can be obtained with a high yield without the need of solvent extraction which involves high cost.

It will be appreciated that the term "process for producing benzene" as used herein is to be understood as a process for producing a product stream comprising benzene. Benzene may be subsequently separated from the product stream comprising benzene. The process for producing benzene according to the invention produces a first product stream comprising benzene and a second product stream comprising benzene. Benzene may be separated from the first product stream and/or the second product stream, as described elsewhere in the description.

As used herein, the term "C # hydrocarbons", wherein "#" is a positive integer, is meant to describe all hydrocarbons having # carbon atoms. Moreover, the term "C #+ hydrocarbons" is meant to describe all hydrocarbon molecules having # or more carbon atoms. Accordingly, the term "C5+ hydrocarbons" is meant to describe a mixture of hydrocarbons having 5 or more carbon atoms.

Step a)

The separation of the source feedstream may be performed e.g. by conventional distillation or absorption. These methods can easily provide a benzene-rich stream and a benzene poor-stream.

Source Feedstream

The alkylbenzenes in the source feedstream may comprise e.g. toluene, ethylbenzene and/or xylene.

The source feedstream used in the process of the present invention is a mixture comprising C5-C12 hydrocarbons, preferably having a boiling point in the range of 30-195° C. Preferably, the feedstream mainly comprises C6-C8 hydrocarbons. Suitable feedstreams include, but are not limited to first stage hydro-treated pyrolysis gasoline, straight run naphtha, hydrocracked gasoline, light coker naphtha and coke oven light oil, FCC gasoline, reformate or mixtures thereof. The source feedstream may have a relatively high sulphur content, such as pyrolysis gasoline (pygas), straight run naphtha, light coker naphtha and coke oven light oil and mixtures thereof. Furthermore, it is preferred that the non-aromatic species comprised in the hydrocarbon feed are saturated (e.g. by prior hydrogenation) in order to reduce the exotherm within the catalyst bed containing the hydrocracking catalyst used in the present process.

This can be achieved by a hydrogenation reactor in series with the hydrocracking reactor or by a reactor comprising a hydrogenation bed and a hydrocracking bed in series or a layer of hydrogenation catalyst on top of the hydrocracking catalyst. The single reactor construction would imply lower capital costs compared to two reactors in series. Accordingly, in preferred embodiments, the first feedstream is subjected to hydrogenation before step (b) and/or the second feedstream is subjected to hydrogenation before step (c).

For instance, a typical composition of first stage hydro-treated pyrolysis gasoline may comprise 10-15 wt-% C5 olefins, 2-4 wt-% C5 paraffins and cycloparaffins, 3-6 wt-% C6 olefins, 1-3 wt-% C6 paraffins and naphthenes, 25-30 wt-% benzene, 15-20 wt-% toluene, 2-5 wt-% ethylbenzene, 3-6 wt-% xylenes, 1-3 wt-% trimethylbenzenes, 4-8 wt-% dicyclopentadiene, and 10-15 wt-% C9+ aromatics, alkyl-styrenes and indenes; see e.g. Table E3.1 from Applied Heterogeneous Catalysis: Design, Manufacture, and Use of Solid Catalysts (1987) J. F. Le Page. However, also hydrocarbon mixtures that are depentanised so the concentrations of all the C6 to C9 hydrocarbon species are relatively high compared with the typical figures above can be advantageously used as a feedstream in the process of the present invention.

In one embodiment, the source feedstream used in the process of the present invention is treated so that it is enriched in mono-aromatic compounds. As used herein, the term "mono-aromatic compound" relates to a hydrocarbon compound having only one aromatic ring. Means and methods suitable to enrich the content of mono-aromatic compounds in a mixed hydrocarbon stream are well known in the art such as the Maxene process; see Bhirud (2002) Proceedings of the DGMK-conference 115-122. The source feedstream used in the process of the present invention may comprise up to 300 wppm of sulphur (i.e. the weight of sulphur atoms, present in any compound, in relation to the total weight of the feed).

The separation of the source feedstream into the first feedstream and the second feedstream may be performed such that the first feedstream comprises C6-hydrocarbons and the second feedstream comprises remaining hydrocarbons. Preferably, however, the separation of the source feedstream into the first feedstream and the second feedstream is performed such that the first feedstream comprises C6-hydrocarbons and at least one of non-aromatic C7 hydrocarbons and the second feedstream comprises remaining hydrocarbons including toluene. Examples of the non-aromatic C7 hydrocarbons include heptane (boiling point=98° C.), methylhexane (boiling point=90° C.), ethylpentane (boiling point=90° C.), 2,4-dimethylpentane (boiling point=90° C.). More examples of C7 alkanes and their boiling points can be found at: http://wwwchem.csustan.edu/chem3012/AlkaneBP.htm Preferably, the separation of the source feedstream into the first feedstream and the second feedstream is performed at a temperature between the boiling point of benzene (80° C.) and the boiling point of toluene (110° C.), i.e. within the range of 80-110° C. More preferably, the separation of the source feedstream into the first feedstream and the second feedstream is performed at a temperature of 85-105° C., for example 90-100° C.

The separation in this range to include non-aromatic C7 hydrocarbons in the first feedstream is advantageous in that the non-aromatic C7 hydrocarbons are hydrocracked to result in useful hydrocarbons such as LPG. Furthermore, a higher proportion of the catalyst for the processing of the second feedstream can be devoted to toluene disproportionation, transalkylation and/or dealkylation. Non-aromatic C7 hydrocarbons tend to rapidly coke conventional toluene disproportionation catalysts.

US2006/0287564 describes a process for increasing the production of benzene from a hydrocarbon mixture including separating a hydrocarbon feedstock into a C6 or lower hydrocarbon stream and a C7 or higher hydrocarbon stream. The C6 or lower hydrocarbon stream is separated into a non-aromatic hydrocarbon stream and an aromatic hydrocarbon stream through a solvent extraction process. The C7 or higher hydrocarbon stream includes non-aromatic C7 hydrocarbons.

Figure 1:
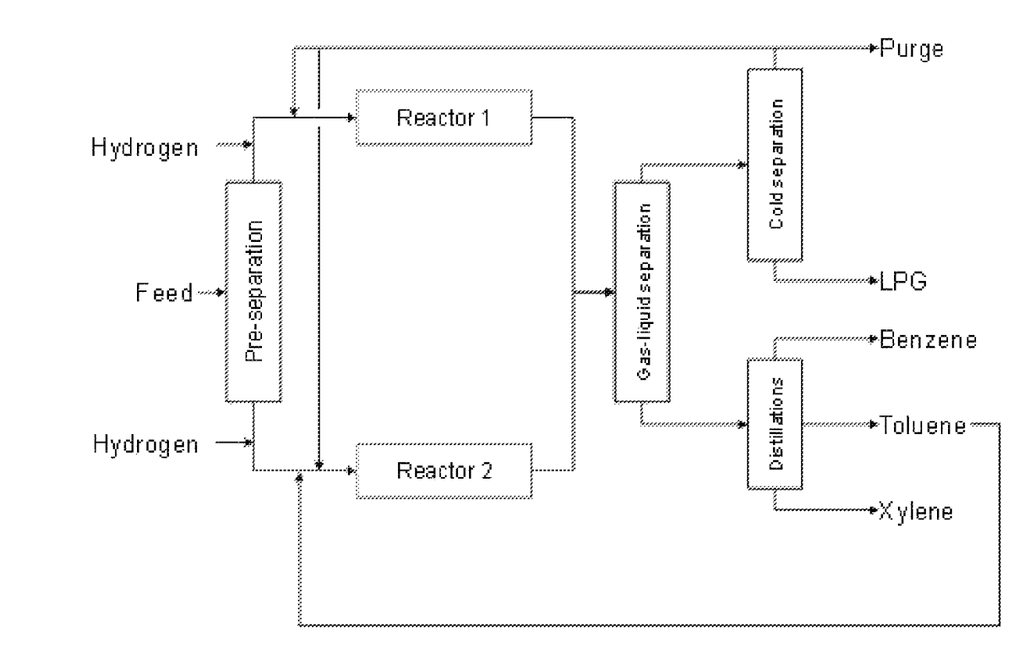
The FIGURE shows a scheme illustrating an example of the process according to the invention.

U.S. Pat. No. 3,957,621 describes a process for processing heavy reformates from which benzene and lighter components have been largely removed. The removed stream (overhead stream at line 12 of FIG. 1) includes the major portion of the benzene in the charge and can include a substantial portion of the toluene (col. 4, l. 65-69).

The first feedstream is contacted with a hydrocracking catalyst in the presence of hydrogen to produce a first hydrocracking stream. The first feedstream comprises benzene and co-boilers of benzene, and smaller proportion of the alkylbenzenes than the source feedstream.

During hydrocracking of hydrocarbons, following reactions influence the proportion of benzene in the product stream:

1. Hydrodealkylation/Benzene Alkylation

The hydrodealkylation of ethylbenzene increases the amount of benzene. This reaction occurs more in a benzene poor stream.

2. Toluene Disproportionation

The toluene disproportionation increases the amount of benzene. This reaction occurs more in a benzene poor stream. The reverse reaction between benzene and xylene reduces the amount of benzene in the product stream. The occurrence of this reaction can be reduced when the stream contains less amount of xylene.

Hence, the separation of the source feed stream into a benzene rich stream with a low amount of xylene and a benzene poor stream with a high amount of toluene results in a higher total amount of benzene produced compared to the cases where no separation takes place.

The first feedstream contains as much as possible of the benzene that was present in the source feedstream. Preferably, the first feedstream contains all benzene that was in the source feedstream. Additionally, this feedstream preferably contains no xylene or trimethylbenzene to avoid any other transalkylation reactions which leads to loss of benzene. Preferably, the first feed stream also contains as little toluene as possible. Toluene in the first feed stream will not result in a benzene loss, but the overall yield of benzene will be higher if the toluene is sent to the second reactor.

Accordingly, the first feed stream preferably comprises at least 55 wt %, at least 60 wt %, at least 70 wt %, at least 80 wt %, at least 90 wt %, at least 95 wt % or 100 wt % of the benzene that was present in the source feedstream.

The second feed stream preferably comprises at most 45 wt %, at most 40 wt %, at most 30 wt %, at most 20 wt %, at most 10 wt %, at most 5 wt % or 0 wt % of benzene that was present in the source feedstream.

The first feed stream preferably comprises at most 45 wt %, at most 40 wt %, at most 30 wt %, at most 20 wt %, at most 10 wt %, at most 5 wt % or 0 wt % of the alkylbenzene that was present in the source feedstream.

The second feed stream preferably comprises at least 55 wt %, at least 60 wt %, at least 70 wt %, at least 80 wt %, at least 90 wt %, at least 95 wt % or 100 wt % of the alkylbenzene that was present in the source feedstream.

The first feed stream preferably comprises at most 45 wt %, at most 40 wt %, at most 30 wt %, at most 20 wt %, at most 10 wt %, at most 5 wt % or 0 wt % of toluene that was present in the source feedstream.

The second feed stream preferably comprises at least 55 wt %, at least 60 wt %, at least 70 wt %, at least 80 wt %, at least 90 wt %, at least 95 wt % or 100 wt % of toluene that was present in the source feedstream.

The first feed stream preferably comprises at most 45 wt %, at most 40 wt %, at most 30 wt %, at most 20 wt %, at most 10 wt %, at most 5 wt % or 0 wt % of xylene that was present in the source feedstream.

The second feed stream preferably comprises at least 55 wt %, at least 60 wt %, at least 70 wt %, at least 80 wt %, at least 90 wt %, at least 95 wt % or 100 wt % of xylene that was present in the source feedstream.

Step b)
Hydrocracking Catalyst

The product produced by the hydrocracking step of the process of the present invention comprises LPG, BTX and methane.

The term "LPG" as used herein refers to the well-established acronym for the term "liquefied petroleum gas". LPG generally consists of a blend of C2-C4 hydrocarbons i.e. a mixture of C2, C3, and C4 hydrocarbons.

The term "BTX" as used herein is well known in the art and relates to a mixture of benzene, toluene and xylenes.

The obtained first product stream is advantageously substantially free from non-aromatic C6+ hydrocarbons due to the catalyst and the conditions employed. Hence, according to the present invention, chemical grade BTX can easily be separated from the first product stream.

After separating BTX from the first product stream, benzene is preferably separated from the BTX. Chemical grade benzene can be easily obtained from the BTX.

Accordingly, in preferred embodiments of the invention, BTX is separated from the first product stream and benzene is separated from the BTX.

Preferably, toluene in the first product stream is recycled back to be included in the second feed stream for a further conversion. This increases the proportion of toluene in the second feed stream and thereby increases the benzene yield in the second product stream.

As used herein, the term "chemical grade BTX" relates to a hydrocarbon mixture comprising less than 5 wt-% hydrocarbons other than benzene, toluene and xylenes, preferably less than 4 wt-% hydrocarbons other than benzene, toluene and xylenes, more preferably less than 3 wt-% hydrocarbons other than benzene, toluene and xylenes, and most preferably less than 2.5 wt-% hydrocarbons other than benzene, toluene and xylenes.

Furthermore, the "chemical grade BTX" produced by the process of the present invention comprises less than 1 wt-% non-aromatic C6+ hydrocarbons, preferably less than 0.7 wt-% non-aromatic C6+ hydrocarbons, more preferably less than 0.6 wt-% non-aromatic C6+ hydrocarbons and most preferably less than 0.5 wt-% non-aromatic C6+ hydrocarbons. The most critical contaminants are the non-aromatic species which have boiling points close to benzene including, but not limited to, cyclohexane, methylcyclopentane, n-hexane, 2-methylpentane and 3-methylpentane.

Accordingly, the first product stream is substantially free from non-aromatic C6+ hydrocarbons. As meant herein, the term "product stream substantially free from non-aromatic C6+ hydrocarbons" means that said product stream comprises less than 1 wt-% non-aromatic C6+ hydrocarbons, preferably less than 0.7 wt-% non-aromatic C6+ hydrocarbons, more preferably less than 0.6 wt-% non-aromatic C6+ hydrocarbons and most preferably less than 0.5 wt-% non-aromatic C6+ hydrocarbons.

According to the present invention, chemical grade benzene can also be easily separated from the first product stream. As used herein, the term "chemical grade benzene" relates to a hydrocarbon stream comprising less than 0.5 wt % hydrocarbons other than benzene.

The term "aromatic hydrocarbon" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

The first product stream produced in the process of the present invention preferably comprises less than 10 wt-% of methane. More preferably, the first product stream produced in the process of the present invention comprises less than 5 wt-% of methane, more preferably less than 4 wt-% of methane, more preferably less than 3 wt-% methane, even more preferably less than 2 wt-% methane, particularly preferably less than 1.5 wt-% methane and most preferably less than 1 wt-% methane.

Preferably, the first product stream is also substantially free from C5 hydrocarbons. As meant herein, the term "product stream substantially free from C5 hydrocarbons" means that said hydrocracking product stream comprises less than 1 wt-% C5 hydrocarbons, preferably less than 0.7 wt-% C5 hydrocarbons, more preferably less than 0.6 wt-% C5 hydrocarbons and most preferably less than 0.5 wt-% C5 hydrocarbons.

The first feed stream can be subjected to hydrodesulphurisation before hydrocracking. Alternatively, the source feed stream can already be subjected to hydrodesulphurisation before the separation step a).

In preferred embodiments, the hydrocracking catalyst further has a hydrodesulphurisation activity. This is advantageous in that it is not necessary to subject the hydrocarbon feedstream to a desulphurisation treatment prior to subjecting said hydrocarbon feedstream to the hydrocracking treatment.

Catalysts having hydrocracking/hydrodesulphurisation activity ("hydrocracking/hydrodesulphurisation catalyst") are described on pages 13-14 and 174 of Hydrocracking Science and Technology (1996) Ed. Julius Scherzer, A. J. Gruia, Pub. Taylor and Francis. Hydrocracking and hydrodesulphurisation reactions proceed through a bifunctional mechanism which requires a relatively strong acid function, which provides for the cracking and isomerization and which provides breaking of the sulphur-carbon bonds comprised in the organic sulfur compounds comprised in the feed, and a metal function, which provides for the olefin hydrogenation and the formation of hydrogen sulfide. Many catalysts used for the hydrocracking/hydrodesulphurisation process are formed by composting various transition metals with the solid support such as alumina, silica, alumina-silica, magnesia and zeolites.

In this context, it is noted that the catalyst used in the processes described in WO 02/44306 A1 and WO 2007/055488 A1 do not utilize a hydrocracking/hydrodesulphurisation catalyst since the presence of the hydrogenation inhibiting secondary metals tin, lead or bismuth render these catalysts unsuitable for hydrodesulphurisation.

The first catalyst is a hydrocracking catalyst comprising 0.01-1 wt-% hydrogenation metal in relation to the total catalyst weight and a zeolite having a pore size of 5-8 Å and a silica ($SiO_2$) to alumina ($Al_2O_3$) molar ratio of 5-200 and the first process conditions comprise a temperature of 425-580° C., a pressure of 300-5000 kPa gauge and a Weight Hourly Space Velocity of 0.1-15 $h^{-1}$ to produce the first product stream comprising benzene.

It is a particular advantage of the process of the invention that the hydrocracking product stream is substantially free from non-aromatic C6+ hydrocarbons as these hydrocarbons usually have boiling points close to the boiling point of C6+ aromatic hydrocarbons. Hence, it can be difficult to separate the non-aromatic C6+ hydrocarbons from the aromatic C6+ hydrocarbons comprised in the hydrocracking product stream by distillation.

These advantageous effects are obtained by strategically selecting the hydrocracking catalyst in combination with the hydrocracking conditions. By combining a hydrocracking catalyst having a relatively strong acid function (e.g. by selecting a catalyst comprising a zeolite having a pore size of 5-8 Å and a silica ($SiO_2$) to alumina ($Al_2O_3$) molar ratio of 5-200) and a relatively strong hydrogenation activity (e.g. by selecting a catalyst comprising 0.01-1 wt-% hydrogenation metal) with process conditions comprising a relatively high process temperature (e.g. by selecting a temperature of 425-580° C.), chemical grade BTX can be produced from a mixed C5-C12 hydrocarbon feedstream, wherein conversion of the benzene comprised in the feedstream to other hydrocarbon compounds such as naphthene compounds is reduced.

The hydrocracking of the feedstream is performed at a pressure of 300-5000 kPa gauge, more preferably at a pressure of 600-3000 kPa gauge, particularly preferably at a pressure of 1000-2000 kPa gauge and most preferably at a pressure of 1200-1600 kPa gauge. By increasing reactor pressure, conversion of C5+ non-aromatics can be increased, but also increases the yield of methane and the hydrogenation of aromatic rings to cyclohexane species which can be cracked to LPG species. This results in a reduction in aromatic yield as the pressure is increased and, as some cyclohexane and its isomer methylcyclopentane, are not fully hydrocracked, there is an optimum in the purity of the resultant benzene at a pressure of 1200-1600 kPa.

The hydrocracking/hydrodesulphurisation of the feedstream is performed at a Weight Hourly Space Velocity (WHSV) of 0.1-15 $h^{-1}$, more preferably at a Weight Hourly Space Velocity of 1-10 $h^{-1}$ and most preferably at a Weight Hourly Space Velocity of 2-9 $h^{-1}$. When the space velocity is too high, not all BTX co-boiling paraffin components are hydrocracked, so it will not be possible to achieve BTX specification by simple distillation of the reactor product. At too low space velocity the yield of methane rises at the expense of propane and butane. By selecting the optimal Weight Hourly Space Velocity, it was surprisingly found that sufficiently complete reaction of the benzene co-boilers is achieved to produce a BTX product of desirable quality without the need for a liquid recycle.

Accordingly, preferred hydrocracking conditions thus include a temperature of 425-580° C., a pressure of 300-5000 kPa gauge and a Weight Hourly Space Velocity of 0.1-15 $h^{-1}$. More preferred hydrocracking conditions include a temperature of 450-550° C., a pressure of 600-3000 kPa gauge and a Weight Hourly Space Velocity of 1-10 $h^{-1}$. Particularly preferred hydrocracking conditions include a temperature of 450-550° C., a pressure of 1000-2000 kPa gauge and a Weight Hourly Space Velocity of 2-9 $h^{-1}$.

Hydrocracking catalysts that are particularly suitable for the process of the present invention comprise a molecular sieve, preferably a zeolite, having a pore size of 5-8 Å.

Zeolites are well-known molecular sieves having a well-defined pore size. As used herein, the term "zeolite" or "aluminosilicate zeolite" relates to an aluminosilicate molecular sieve. An overview of their characteristics is for example provided by the chapter on Molecular Sieves in Kirk-Othmer Encyclopedia of Chemical Technology, Volume 16, p 811-853; in Atlas of Zeolite Framework Types, 5th edition, (Elsevier, 2001). Preferably, the hydrocracking catalyst comprises a medium pore size aluminosilicate zeolite or a large pore size aluminosilicate zeolite. Suitable zeolites include, but are not limited to, ZSM-5, MCM-22, ZSM-11, beta zeolite, EU-1 zeolite, zeolite Y, faujastite, ferrierite and mordenite. The term "medium pore zeolite" is commonly used in the field of zeolite catalysts. Accordingly, a medium pore size zeolite is a zeolite having a pore size of about 5-6 Å. Suitable medium pore size zeolites are 10-ring zeolites, i.e. the pore is formed by a ring consisting of 10 $SiO_4$ or $AlO_4$ tetrahedra. Suitable large pore size zeolites have a pore size of about 6-8 Å and are of the 12-ring structure type. Zeolites of the 8-ring structure type are called small pore size zeolites. In the above cited Atlas of Zeolite Framework Types various zeolites are listed based on ring structure. Most preferably the zeolite is ZSM-5 zeolite, which is a well-known zeolite having MFI structure. ZSM-5 zeolite is preferred for the high purity of BTX.

Preferably, the silica to alumina ratio of the ZSM-5 zeolite is in the range of 20-200, more preferably in the range of 30-100.

The zeolite is in the hydrogen form: i.e. having at least a portion of the original cations associated therewith replaced by hydrogen. Methods to convert an aluminosilicate zeolite to the hydrogen form are well known in the art. A first method involves direct ion exchange employing an acid and/or salt. A second method involves base-exchange using ammonium salts followed by calcination.

Furthermore, the catalyst composition comprises a sufficient amount of hydrogenation metal to ensure that the catalyst has a relatively strong hydrogenation activity. Hydrogenation metals are well known in the art of petrochemical catalysts.

It is preferred that the catalyst does not comprise secondary metals, such as tin, lead or bismuth, that inhibit the hydrogenation activity of the hydrogenation metal. Preferably, the hydrocracking catalyst used in the process of the present invention (the first hydrocracking catalyst and the second hydrocracking catalyst) accordingly comprises less than 0.01 parts tin and less than 0.02 parts lead and less than 0.01 parts bismuth (on the basis of 100 parts by weight of the total catalyst), preferably less than 0.005 parts tin and less than 0.01 parts lead and less than 0.005 parts bismuth (on the basis of 100 parts by weight of total catalyst).

The catalyst composition preferably comprises 0.01-1 wt-% hydrogenation metal, more preferably 0.01-0.7 wt-%, more preferably 0.01-0.5 wt-% hydrogenation metal, more preferably 0.01-0.3 wt-%. The catalyst composition may more preferably comprise 0.01-0.1 wt-% or 0.02-0.09 wt-% hydrogenation metal. In the context of the present invention, the term "wt %" when relating to the metal content as comprised in a catalyst composition relates to the wt % (or "wt-%") of said metal in relation to the weight of the total catalyst, including catalyst binders, fillers, diluents and the like. Preferably, the hydrogenation metal is at least one element selected from Group 10 of the periodic table of Elements. The preferred Group 10 element is platinum.

Accordingly, the hydrocracking catalyst used in the process of the present invention comprises a zeolite having a pore size of 5-8 Å, a silica ($SiO_2$) to alumina ($Al_2O_3$) molar ratio of 5-200 and 0.01-1 wt-% platinum (in relation to the total catalyst).

The hydrocracking catalyst composition may further comprise a binder. Alumina ($Al_2O_3$) is a preferred binder. The catalyst composition of the present invention preferably comprises at least 10 wt-%, most preferably at least 20 wt-% binder and preferably comprises up to 40 wt-% binder. In one embodiment, the hydrogenation metal is deposited on the binder, which preferably is $Al_2O_3$. In some embodiments, the catalyst composition of the present invention comprises little or no binder, for example less than 2 wt %, less than 1 wt %, less than 0.5 wt % or 0 wt %.

According to one embodiment of the invention the hydrocracking catalyst is a mixture of the hydrogenation metal on a support of an amorphous alumina and the zeolite.

According to another embodiment of the invention the hydrocracking catalyst comprises the hydrogenation metal on a support of the zeolite. In this case, the hydrogenation metal and the zeolite giving cracking functions are in closer proximity to one another which translates into a shorter diffusion length between the two sites. This allows high space velocity, which translates into smaller reactor volumes and thus lower CAPEX. Accordingly, in some preferred embodiments, the hydrocracking catalyst is the hydrogenation metal on a support of the zeolite and step (b) is performed at a Weight Hourly Space Velocity of 10-15 $h^{-1}$.

The hydrocracking step is performed in the presence of an excess of hydrogen in the reaction mixture. This means that a more than stoichiometric amount of hydrogen is present in the reaction mixture that is subjected to hydrocracking. Preferably, the molar ratio of hydrogen to hydrocarbon species ($H_2$/HC molar ratio) in the reactor feed is between 1:1 and 4:1, preferably between 1:1 and 3:1 and most preferably between 1:1 and 2:1. A higher benzene purity in the product stream can be obtained by selecting a relatively low $H_2$/HC molar ratio. In this context the term "hydrocarbon species" means all hydrocarbon molecules present in the reactor feed such as benzene, toluene, hexane, cyclohexane etc. It is necessary to know the composition of the feed to then calculate the average molecular weight of this stream to be able to calculate the correct hydrogen feed rate. The excess amount of hydrogen in the reaction mixture suppresses the coke formation which is believed to lead to catalyst deactivation.

Separation of BTX from the First Product Stream and Benzene from Toluene/Xylene

The first product stream may be subjected to separation by standard means and methods suitable for separating methane and unreacted hydrogen comprised in the first product stream as a first separate stream, the LPG comprised in the first product stream as a second separate stream and the BTX as a third separate stream. Preferably, the BTX is separated from the hydrocracking product stream by gas-liquid separation or distillation. One non-limiting example of such a separation method includes a series of distillation steps. The first distillation step at moderate temperature separates most of the aromatic species (liquid product) from the hydrogen, $H_2S$, methane and LPG species. The gaseous stream from this distillation is further cooled (to about −30° C.) and distilled again to separate the remaining aromatics species and most of the propane and butane. The gaseous product (mainly hydrogen, $H_2S$, methane and ethane) is then further cooled (to about −100° C.) to separate the ethane and leave the hydrogen, $H_2S$ and methane in the gaseous stream that will be recycled to the reactor. To control the levels of $H_2S$ and methane in the reactor feed, a proportion of recycle gas is removed from the system as a purge. The quantity of material that is purged depends on the levels of methane and $H_2S$ in the recycle stream which in-turn depend on the feed composition. The purge stream will have the same composition as the recycle stream. As the purge will contain mainly hydrogen and methane it is suitable for use as a fuel gas or may be further treated (e.g. via a pressure swing adsorption unit) to separately recover a high purity hydrogen stream and a methane/$H_2S$ stream which can be used as a fuel gas. Preferably, after the BTX is separated from the first product stream, benzene, toluene and xylene are separated from each other by distillation.

Step c)

The second feedstream is converted to a second product stream under hydrocarbon conversion conditions selected from the group consisting of hydrocracking, toluene disproportionation and hydrodealkylation.

After the conversion, the BTX may be separated from the second product stream. Methods and means suitable for the separation of BTX from the second product stream are the same as described for the separation of BTX from the first product stream or the combined product stream. Benzene may be separated from the BTX by known methods as described above in relation to step b). Toluene and xylene may be separated from each other by known methods as described above in relation to step b). Toluene in the second product stream may be recycled back to be included in the second feed stream.

In the cases where step c) involves option i), the BTX may be separated from the second product stream and benzene may be separated from the BTX to obtain chemical grade benzene. Alternatively, the second product stream is combined with the first product stream to obtain a combined stream, the BTX is separated from the combined stream and benzene is separated from the BTX to obtain chemical grade benzene. Accordingly, in some preferred embodiments of the process of the invention, step c) involves option i) and the BTX is separated from the second product stream optionally after the second product stream is mixed with the first product stream, and benzene is separated from the BTX.

In the cases where step c) involves option ii) or iii), BTX obtained from the second product stream is not chemical grade BTX. This BTX may be directly used as a final product. Alternatively, the benzene separated from the BTX separated from the second product stream may be recycled back to be included in the first product stream.

Alternatively, the second product stream may be recycled back to be included in the source feed stream without a separation of BTX from the second product stream.

Hydrocracking

In some preferred embodiments, the second process conditions are chosen suitable for hydrocracking and a second catalyst suitable for hydrocracking is used. Suitable catalyst may be the same as the catalysts as described in detail for step b). Suitable process conditions may be the same as the process conditions as described in detail for step b). The obtained second product stream is advantageously substantially free from non-aromatic C6+ hydrocarbons due to the catalyst and the conditions employed.

Preferably, the proportion of benzene in the total amount of BTX in the second feed stream is at most 10 wt %. This increases the proportion of benzene in the second product stream.

When the feed stream has a lower proportion of benzene, more hydrodealkylation and toluene disproportionation occur, which increase the proportion of the obtained benzene.

Hydrodealkylation

In some preferred embodiments, the second process conditions are chosen suitable for hydrodealkylation.

It has been previously described that benzene of very high purity can be prepared by hydrodealkylation of a feedstream comprising aliphatic and aromatic hydrocarbons. Hydrodealkylation processes for the preparation of benzene are commercially used, for instance for converting the C6-C9 fraction of pyrolysis products obtained in steam crackers to benzene; see e.g. Handbook of Commercial Catalysts: Heterogeneous Catalysts ed. Howard F. Rase (2000) CRC Press p. 211-212 and Handbook of Petroleum Refining Processes ed. Robert A. Meyers (1986) Mcgraw-Hill p 2-3-2-7. The prior art discloses hydrodealkylation processes wherein the formation of methane is reduced. Such a process is described in WO 2008/015027 which provides a catalytic hydrodealkylation process using a catalyst consisting of a ZSM-5 catalyst having a Si/Al molar ratio of 5-100, platinum and molybdenum. In the hydrodealkylation process according to WO 2008/015027 A1 the process conditions are selected as such that the formation of methane is reduced.

WO 2010/102712 A2 describes a method for obtaining essentially pure benzene by hydrodealkylation wherein the non-aromatic hydrocarbons are removed from the stream that is fed to the hydrodealkylation reactor by extractive distillation.

Processes for hydrodealkylation of hydrocarbon mixtures comprising C6-C9 aromatic hydrocarbons are well known in the art and include thermal hydrodealkylation and catalytic hydrodealkylation; see e.g. WO 2010/102712 A2. Catalytic hydrodealkylation is preferred in the context of the present invention as this hydrodealkylation process generally has a higher selectivity towards benzene than thermal hydrodealkylation. Preferably catalytic hydrodealkylation is employed, wherein the hydrodealkylation catalyst is selected from the group consisting of supported chromium oxide catalyst, supported molybdenum oxide catalyst, platinum on silica or alumina and platinum oxide on silica or alumina.

The process conditions useful for hydrodealkylation, also described herein as "hydrodealkylation conditions", can be easily determined by the person skilled in the art. The process conditions used for thermal hydrodealkylation are for instance described in DE 1668719 A1 and include a temperature of 600-800° C., a pressure of 3-10 MPa gauge and a reaction time of 15-45 seconds. The process conditions used for the preferred catalytic hydrodealkylation are described in and preferably include a temperature of 500-650° C., a pressure of 3.5-7 MPa gauge and a Weight Hourly Space Velocity of 0.5-2 $h^{-1}$; see also Handbook of Commercial Catalysts: Heterogeneous Catalysts ed. Howard F. Rase (2000) Loc. cit.

The hydrodealkylation product stream is typically separated into a liquid stream (containing benzene and other aromatics species) and a gas stream (containing hydrogen, $H_2S$, methane and other low boiling point hydrocarbons) by a combination of cooling and distillation. The liquid stream may be further separated, by distillation, into a benzene stream, a C7 to C9 aromatics stream and a heavy aromatic stream. The C7 to C9 aromatic stream may be recycled back to the hydrodealkylation reactor section as a recycle to increase overall conversion and benzene yield. The heavy aromatic stream, which contains polyaromatic species such as byphenyl, is preferably not recycled to the reactor but may be exported as a separate product stream. The gas stream contains significant quantities of hydrogen may be recycled back, via a recycle gas compressor, to the reactor section. A recycle gas purge may be used to control the concentrations of methane and $H_2S$ in the reactor feed.

Toluene Disproportionation

In some preferred embodiments, the second catalyst and the second process conditions are chosen suitable for toluene disproportionation.

This is particularly advantageous when the second feedstream comprises a relatively high proportion of toluene.

Catalysts and process conditions suitable for toluene disproportionation are well-known and described in detail e.g. in T.-C. Tsai et al., Applied Catalysis A: General 181 (1999) 355-398. Summary of commercial toluene disproportionation processes is described in Table 4 of this publication. Further examples of catalysts and process conditions suitable for toluene disproportionation are mentioned e.g. in U.S. Pat. Nos. 6,977,320, 6,504,074 and 6,160,191.

The catalyst may e.g. comprise zeolite as described above in relation to the hydrocracking catalyst.

For example, preferably, the process conditions comprise a temperature in the range of between 400° C. to 550° C., at a pressure in the range of from 1 to 100 atmospheres and at a weight hourly space velocity in the range of from 0.5 to 50 $hr^{-1}$. More typically, the process conditions comprise a temperature in the range of between 400° C. to 500° C., at a pressure in the range of from 10 to 50 atmospheres and at a weight hourly space velocity in the range of from 1 to 10 $hr^{-1}$ The present invention further provides a process in which the source feedstream is be separated into a first feedstream comprising a higher proportion of benzene than the source feedstream, a second feedstream comprising a lower proportion of benzene than the source feedstream and a higher proportion of toluene than the source feedstream and a lower proportion of xylene than the source feedstream and a third feedstream comprising a lower proportion of benzene than the source feedstream, a lower proportion of toluene than the source feedstream and a higher proportion of xylene than the source feedstream.

The third feedstream may be contacted with hydrogen under third process conditions to produce a third product stream comprising benzene. The third process conditions may be the conditions as described for option iii) in relation to the second process conditions for step (c).

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is noted that the term "comprising" does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention will now be elucidated by the following non-limiting Examples.

The FIGURE shows a scheme illustrating an example of the process according to the invention. In this example, the source feed stream is separated by a pre-separation means to a first feed stream rich in benzene and a second feed stream poor in benzene. The first feed stream is contacted with hydrogen in the presence of a hydrocracking catalyst in reactor 1. The second feed stream is also contacted with hydrogen in hydrocracking conditions in reactor 2. The hydrocracking product streams comprising LPG and BTX are subjected to gas-liquid separation to be separated into LPG and BTX. BTX is separated into benzene, toluene and xylene. Toluene is recycled back to the second feed stream.

Experiments

Feed mixtures comprising different compositions of hydrocarbons were subjected to hydrocracking in order to determine the influence of the feed compositions to the product compositions.

In experiment 1, a feed stream having a composition typical for pyrolysis gasoline was subjected to hydrocracking. This corresponds to an example of the conventional process where no pre-separation of the feedstream is performed before hydrocracking.

In experiment 2, a feed stream comprising a high amount of benzene and substantially no amount of alkylbenzene was subjected to hydrocracking. This corresponds to an example of the hydrocracking of the first feed stream of step b) of the process of the present invention.

In experiment 3, a feed stream comprising no benzene and consisting of toluene was subjected to hydrocracking. This corresponds to an example of the hydrocracking of the second feed stream of step c) i) of the process of the present invention.

In experiment 4, a feed stream comprising no benzene and large amounts of toluene, xylene and ethylbenzene was subjected to hydrocracking. This corresponds to a further example of the hydrocracking of the second feed stream of step c) i) of the process of the present invention.

Experiment 1

Two-stage hydrotreated pyrolysis gasoline having the composition shown in Table 1 was fed to a reactor having a hydrocracking catalyst of 0.03 wt % of Pt deposited on ZSM-5, where the ratio of $SiO2/Al2O3$ is 80. The process conditions were 476° C., 200 psig, H2/HC=3, WHSV=2 $hr^{-1}$. The composition of the resulting product stream is shown in Table 1.

Benzene purity of the product stream is extremely high, i.e. there is substantially no co-boilers of benzene.

However, the amount of benzene in the product stream is not higher than the source feedstream. A substantial amount of alkylbenzene, particularly toluene and xylene is obtained.

TABLE 1

|  | Source (wt %) | Product (wt %) |
| --- | --- | --- |
| Benzene | 48.11 | 47.75 |
| Cyclohexane | 2.87 | 0.01 |
| Toluene | 16.03 | 19.22 |
| Mixed xylenes | 2.83 | 2.85 |
| Ethylbenzene | 5.61 | 0.11 |
| Trimethylbenzene | 0.03 | 0.03 |
| Benzene purity | 71.14% | 99.96% |

Benzene purity is defined as [mass of benzene]/[sum of the masses of benzene, 2-methylpentane, 3-methylpentane, hexane, methylcyclopentane and cyclohexane] in Tables 1-4.

Experiment 2: Benzene-Rich Stream

A feed having the composition shown in Table 2 was fed to a reactor comprising a hydrocracking catalyst having the same composition as the catalyst used in experiment 1. The process conditions were 470° C., 200 psig, H2/HC=1, WHSV=3 hr$^{-1}$. The composition of the resulting product stream is shown in Table 2.

This experiment shows that hydrocracking a source feedstream comprising a high amount of benzene results in some loss of benzene, but chemical grade BTX is obtained from which a large amount of chemical grade benzene can be obtained.

TABLE 2

|  | Source (wt %) | Product (wt %) |
| --- | --- | --- |
| Benzene | 75.36 | 71.57 |
| Cyclohexane | 0 | 0.01 |
| Toluene | 0 | 3.13 |
| Mixed xylenes | 0 | 0.18 |
| Ethylbenzene | 0 | 0.25 |
| Trimethylbenzene | 0 | 0.01 |
| Benzene purity | 78.91% | 99.83% |

Experiment 3: Benzene-Poor Stream

A feed having the composition shown in Table 3 was fed to a reactor comprising a hydrocracking catalyst having the same composition as the catalyst used in experiment 1. The process conditions were 450° C., 200 psig, H2/HC=1, WHSV=3 hr$^{-1}$. The composition of the resulting product stream is shown in Table 3.

This experiment illustrates the effect of hydrocracking a feed stream with a low benzene content. It can be seen that a substantial amount of toluene converted into benzene and toluene by toluene disproportionation.

TABLE 3

|  | Source (wt %) | Product (wt %) |
| --- | --- | --- |
| Benzene | 0 | 8.88 |
| Cyclohexane | 0 | 0 |
| Toluene | 100 | 78.25 |
| Mixed xylenes | 0 | 11.26 |
| Ethylbenzene | 0 | 0.01 |
| Trimethylbenzene | 0 | 0.05 |
| Benzene purity | — | 99.96% |

Experiment 4: Benzene-Poor Stream

A feed having the composition shown in Table 4 was fed to a reactor comprising a hydrocracking catalyst having the same composition as the catalyst used in experiment 1. The process conditions were 450° C., 200 psig, H2/HC=1, WHSV=3 hr$^{-1}$. The composition of the resulting product stream is shown in Table 4.

TABLE 4

|  | Source (wt %) | Product (wt %) |
| --- | --- | --- |
| Benzene | 0 | 20.16 |
| Cyclohexane | 0 | 0.01 |
| Toluene | 65.0 | 56.47 |
| Mixed xylenes | 12.2 | 15.83 |
| Ethylbenzene | 22.7 | 0.04 |
| Trimethylbenzene | 0 | 0.11 |
| Benzene purity | — | 99.96% |

In this experiment, a feed comprising substantially no components other than alkyl aromatics (toluene, xylene and ethylbenzene) was hydrocracked. This experiment clearly demonstrates that the presence of xylenes limits toluene disproportionation/benzene formation. Substantially all ethylbenzene was converted to benzene, which resulted in the difference in the benzene contents between examples 3 and 4.

The invention claimed is:

1. A process for producing benzene comprising the steps of:
   (a) separating a source feedstream comprising C5-C12 hydrocarbons including benzene and alkylbenzenes into:
      a first feedstream comprising C6-hydrocarbons comprising benzene and at least one non-aromatic C7 hydrocarbon, and
      a second feedstream comprising remaining hydrocarbons including toluene;
   (b) contacting the first feedstream in the presence of hydrogen with a first hydrocracking catalyst comprising 0.01-1 wt-% hydrogenation metal in relation to the total catalyst weight and a zeolite having a pore size of 5-8 Å and a silica to alumina molar ratio of 5-200 under first process conditions to produce a first product stream comprising benzene, wherein the first process conditions include a temperature of 425-580° C., a pressure of 300-5000 kPa gauge and a Weight Hourly Space Velocity of 0.1-15 h$^{-1}$;
   (c) contacting the second feedstream in the presence of hydrogen with a second hydrocracking catalyst comprising 0.01-1 wt-% hydrogenation metal in relation to the total catalyst weight and a zeolite having a pore size of 5-8 Å and a silica to alumina molar ratio of 5-200 under second process conditions which include a temperature of 300-600° C., a pressure of 300-5000 kPa gauge and a Weight Hourly Space Velocity of 0.1-15 h$^{-1}$, wherein contacting the second feedstream in the presence of hydrogen with the second hydrocracking catalyst under the second process conditions produces a second product stream comprising benzene and less than 1 wt-% non-aromatic C6+ hydrocarbons;
   (d) combining the second product stream with the first product stream to obtain a combined product stream;
   (e) separating BTX from the combined product stream, and
   (f) separating a benzene stream comprising less than 0.5 wt % hydrocarbons other than benzene from the BTX.

2. The process according to claim 1, wherein the first hydrocracking catalyst comprises less than 0.01 parts tin, less than 0.02 parts lead and less than 0.01 parts bismuth on the basis of 100 parts by weight of the total catalyst.

3. The process according to claim 1, wherein the first feedstream is subjected to hydrogenation before step (b) and/or the second feedstream is subjected to hydrogenation before step (c).

4. The process according to claim 1, wherein the source feedstream comprises pyrolysis gasoline, straight run naphtha, light coker naphtha, coke oven light oil, or mixtures thereof.

5. The process according to claim 1, wherein the second feedstream includes BTX and the proportion of benzene in a total amount of BTX in the second feedstream is at most 10 wt %.

6. The process according to claim 1, wherein the second product stream comprises less than 0.7 wt-% non-aromatic C6+ hydrocarbons.

7. The process according to claim 1, wherein the second product stream comprises less than 0.6 wt-% non-aromatic C6+ hydrocarbons.

8. The process according to claim 1, wherein the first product stream comprises less than 1.0 wt-% non-aromatic C6+ hydrocarbons.

9. The process according to claim 1, wherein the first product stream comprises less than 0.7 wt-% non-aromatic C6+ hydrocarbons.

10. The process according to claim 1, wherein the first product stream comprises less than 0.6 wt-% non-aromatic C6+ hydrocarbons.

11. The process according to claim 1, wherein the first product stream comprises less than 1.0 wt-% non-aromatic C5 hydrocarbons.

12. The process according to claim 1, wherein the first product stream comprises less than 0.7 wt-% non-aromatic C5 hydrocarbons.

13. The process according to claim 1, wherein the first product stream comprises less than 0.6 wt-% non-aromatic C5 hydrocarbons.

* * * * *